(12) United States Patent
Xie et al.

(10) Patent No.: US 11,434,324 B2
(45) Date of Patent: Sep. 6, 2022

(54) ORGANIC POLYSPIROGRID NANO POLYMER MATERIAL AND PREPARATION METHOD THEREFOR

(71) Applicant: NANJING UNIVERSITY OF POSTS & TELECOMMUNICATIONS, Jiangsu (CN)

(72) Inventors: Linghai Xie, Jiangsu (CN); Lei Tang, Jiangsu (CN); Ying Wei, Jiangsu (CN); Wei Huang, Jiangsu (CN)

(73) Assignee: NANJING UNIVERSITY OF POSTS & TELECOMMUNICATIONS, Jiangsu (CN)

( * ) Notice: Subject to any disclaimer, the term of this patent is extended or adjusted under 35 U.S.C. 154(b) by 186 days.

(21) Appl. No.: 16/758,870

(22) PCT Filed: Jul. 13, 2018

(86) PCT No.: PCT/CN2018/095689
§ 371 (c)(1),
(2) Date: Apr. 24, 2020

(87) PCT Pub. No.: WO2019/080550
PCT Pub. Date: May 2, 2019

(65) Prior Publication Data
US 2020/0362093 A1    Nov. 19, 2020

(30) Foreign Application Priority Data

Oct. 25, 2017  (CN) .......................... 201711007986.5

(51) Int. Cl.
*C08G 61/02* (2006.01)
*C07D 495/20* (2006.01)
*C07D 495/22* (2006.01)

(52) U.S. Cl.
CPC .......... *C08G 61/02* (2013.01); *C07D 495/20* (2013.01); *C07D 495/22* (2013.01); *C08G 2261/11* (2013.01)

(58) Field of Classification Search
CPC ................ C07D 471/22; C08G 61/124; C08G 2261/18; C08G 2261/3142; C08G 2261/3241; C08G 2261/45; B82Y 30/00
See application file for complete search history.

(56) References Cited

U.S. PATENT DOCUMENTS

2006/0183042 A1    8/2006  Huang et al.

FOREIGN PATENT DOCUMENTS

| CN | 101213238 | 7/2008 |
|---|---|---|
| CN | 102167800 | 8/2011 |

(Continued)

OTHER PUBLICATIONS

"International Search Report (Form PCT/ISA/210) of PCT/CN2018/095689," dated Oct. 18, 2018, with English translation thereof, pp. 1-5.

*Primary Examiner* — Shane Fang
(74) *Attorney, Agent, or Firm* — JCIP Global Inc.

(57) ABSTRACT

The invention relates to an organic polyspiralgrid nanopolymer material and a preparation method thereof, and belongs to the field of nanotechnology and organic electronics. The structure of the organic polyspiralgrid nanopolymer material is composed of grids containing a spiro ring that serves as a repeat unit to form a special nano polymer, and the structure shares the spiro ring structure. A synthetic method thereof relates to a synthon containing the spiro ring, and by means of a Friedel-Crafts reaction, an organic spirogrid and a nano polymer thereof are built. By means of reasonable molecular design and the Friedel-Crafts reaction with the advantages of being mild in reaction condition, high in yield, high in selectivity, simple in posttreatment, green, (Continued)

free of toxicity and the like, the problems that a traditional polymer molecule is complex in synthesis step, toxic in posttreatment, large in pollution and the like are solved.

5 Claims, 8 Drawing Sheets

(56) References Cited

FOREIGN PATENT DOCUMENTS

| | | |
|---|---|---|
| CN | 103965438 | 8/2014 |
| CN | 107892695 | 4/2018 |
| CN | 107915746 | 4/2018 |
| WO | 2004020373 | 3/2004 |

| Gel chromatogram analysis | Number-average molecular weight (Mn) | Weight-average molecular weight (Mw) | Dispersion index (PDI) | Repeated units |
|---|---|---|---|---|
| 4a | $1.11 \times 10^5$ | $1.61 \times 10^5$ | 1.45 | 104 |

ORGANIC POLYSPIROGRID NANO POLYMER MATERIAL AND PREPARATION METHOD THEREFOR

CROSS-REFERENCE TO RELATED APPLICATION

This application is a 371 of international application of PCT application serial no. PCT/CN2018/095689, filed on Jul. 13, 2018, which claims the priority benefit of China application no. 201711007986.5, filed on Oct. 25, 2017. The entirety of each of the above mentioned patent applications is hereby incorporated by reference herein and made a part of this specification.

BACKGROUND OF THE INVENTION

1. Technical Field

The present invention relates to a type of organic polyspiralgrid nanopolymer material and its preparation method and belongs to the field of nanotechnology and organic electronics.

2. Background Art

Organic small molecules, oligomers, conjugated polymers and stacked polymers have now undergone decades of development. Studies have shown that molecules with these structures have good molecular solubility and clear molecular weight and are easily purified. Nanoscale molecules with closed-loop structures, such as polyrotaxane and polyporphyrin, also have higher thermal stability, chemical stability and mechanical stability than traditional linear structures. This also gives them a great potential of application in organic semiconductor materials.

The key to building molecules with a closed-loop structure at the nanoscale lies in the nanoscale closed-loop structural unit and the nano-connection. Most of the nanoscale structural units are closed-loop structures with extended sites, including rotanes, porphyrins and cyclosiloxanes. On the other hand, the way in which nanoscale structural units are interconnected is called nano-connection. In general, nano-connections are divided into non-covalent bond connections and the covalent bond connections. Non-covalent bond connections mainly include supramolecular interactions and coordination connections. Compared with non-covalent bond connections, covalent bond connections have better stability and a clearer spatial extension direction, so they have better designability. Nanoscale structures currently connected by covalent bonds include polyrotaxane (J. J. Michels, M. J. O'Connell, P. N. Taylor, J. S. Wilson, F. Cacialli and H. L. Anderson, *Chem. Eur. J.* 2003, 9, 6167-6176), linear polyporphyrin (M. Hutin, J. K. Sprafke, B. Odell, H. L. Anderson, T. D. W. Claridge, *J. Am. Chem. Soc.* 2013, 135, 12798-12807), belt-like polyporphyrin (H. Mori, T. Tanaka, S. Lee, J. M. Lim, D. Kim, and A. Osuka, *J. Am. Chem. Soc.* 2015, 137, 2097-2106), ladder-like polysiloxane (K. W. Krantz, Journal of Organometallic c 695 (2010) 1363-1369), etc. However, most of the known nanoscale structural units have irregularities. The irregularity of the monomers and the large steric hindrance of the nanostructures increase the difficulty of nano-connection, resulting in a low degree of polymerization in polymers with nanoscale structural units. Therefore, achieving the efficient preparation of regular monomers and increasing the connectivity between nano-monomers are two crucial factors for the synthesis of polymers with large molecular weights.

In 2014, Prof. Xie Linghai's research group proposed a novel structurally rigid nanoscale three-dimensional closed-loop structure—organic nanogrid (L. Wang, G.-W. Zhang, C.-J. Ou, L.-H. Xie, J.-Y. Lin, Y.-Y. Liu and W. Huang, *Org. Lett.*, 2014, 16, 1748-1751). Such nanogrid has clear edges and vertices, active sites, and flexible, complex 1D, 2D and 3D network structures which can be used to build structure. According to their geometric structures, nanogrids can be divided into trapezoidal, pinwheel-shaped and rhombic nanogrids. Because nanogrids have multiple connection points, each type of nanogrids has its own unique connection. For example, trapezoidal nanogrids can not only build ordinary non-conjugated nano-polygrids through C—C coupling (Suzuki or Yamamoto) reaction (Q.-Y. Feng, Y.-L. Han, M.-N. Yu, B. Li, Y. Wei, L.-H Xie and W. Huang, *Chin. J. Polym. Sci*, 2017, 35, 87-97), but also construct trapezoidal polygrid. The rhombic interconnections among rhombic nanogrids can form rhombic polygrids. Compared with the non-conjugated nano-polygrid connected with the carbon-carbon single bond, the trapezoidal polygrid and rhombic polygrid connected with carbon-carbon double bonds have good rigidity and can avoid the structural configuration complexity caused by the rotation of the bonds. The synthesis of rhombic polygrids now is to link rhombic mono-nanogrids together through non-covalent bonds. However, constructing rhombic polygrids with covalent bonds has not been reported to date.

In order to synthesize covalently bonded rhombic polygrids, we need to design and synthesize a type of potential rhombic nano-synthons with multiple active sites. With these requirements in mind, we chose spiral ring aromatics as the central (cross) building block. Spiral ring aromatics have at least four reaction sites and they are cross-like compounds in structure. This is essential for them as the connection block to build rhombic nanogrids. As for the preparation of the above organic nano rhombic polygrids, the present invention has achieved the effective preparation of spiral ring organic nano rhombic mono-grids through a series of L-type synthons containing spiral cycles based on Friedel-Crafts reaction. Such spiral ring-containing organic nano rhombic mono-grids are called organic mono-spiralgrids. On this basis, we have developed Friedel-Crafts reactions among different spiral ring-containing synthons and prepared organic polyspiralgrid nanopolymers having environmental friendliness and atomic economy without metal catalysis. Such materials can be applied to organic light-emitting devices, organic solar cells and organic transistor memories, so they have broad development prospects.

SUMMARY OF THE INVENTION

Technical Problem: The present invention aims to propose a type of organic polyspiralgrid nanopolymer material as well as its preparation method. Through reasonable molecular design, it utilizes the advantages of Friedel-Crafts reaction, such as mild reaction conditions, high yield, high selectivity, easy post-treatment, and green and non-toxicity, but overcomes the disadvantages of traditional polymer synthesis methods, such as complex synthesis steps, toxic post-treatment and heavy pollution. By using the sp3 carbon of fluorene to link various types of organic groups, it can accurately synthesize structurally complicated polymer materials having an expandable space and then prepare the corresponding functional organic nanopolymers with them.

Technical solution: The present invention involves a type of organic polyspiralgrid nanopolymer material. The structure of the material contains at least two types of fluorene-like groups, of which one is a 9-phenylfluorenol derivative and the other is a spiral ring structure with a geometric configuration similar to that of spirobifluorene. Its structural formula is as follows:

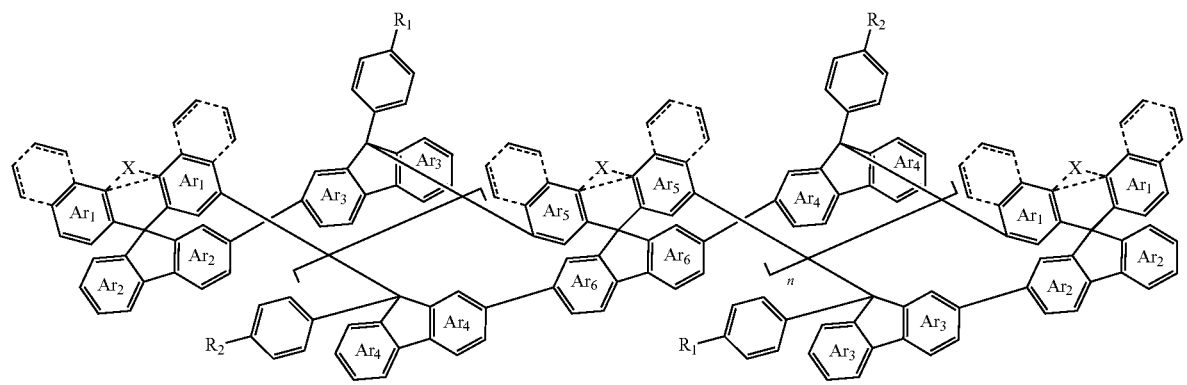
wherein, $R_1$ and $R_2$ are identical or different, and they are common alkyl chains.
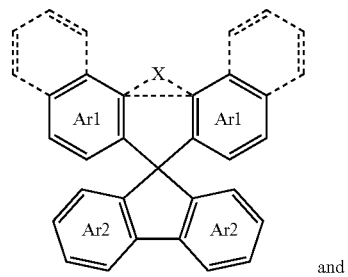
and
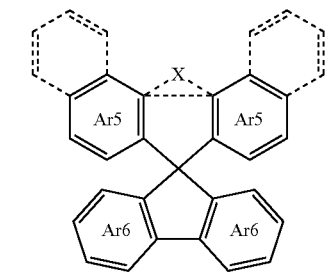
are identical or different and are common fluorene-like spiral ring compounds. Their specific structures are as follows:
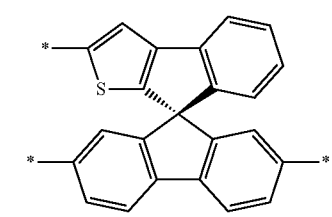
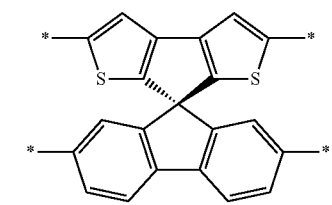
-continued
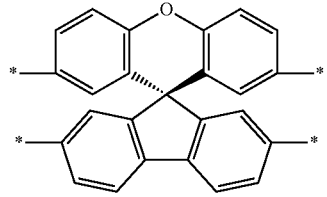
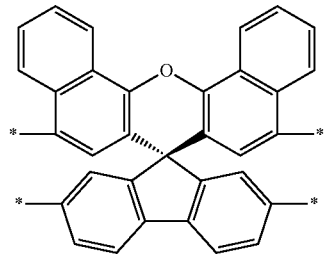
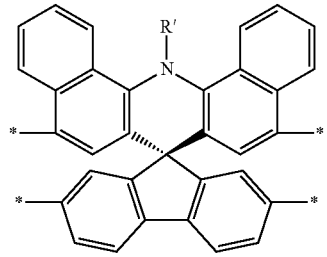
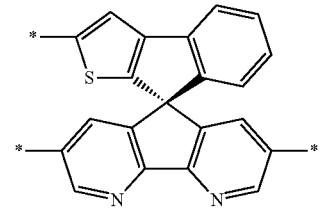
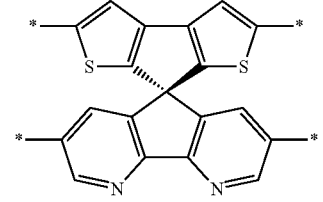

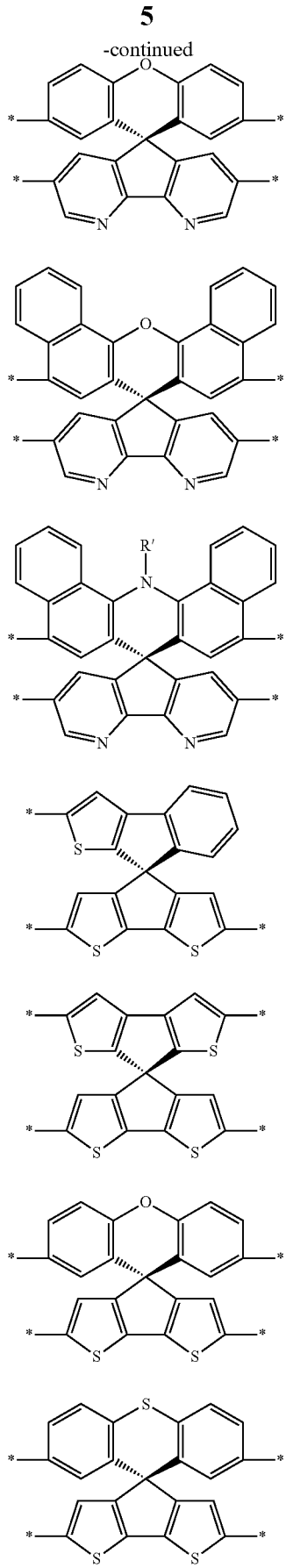

-continued

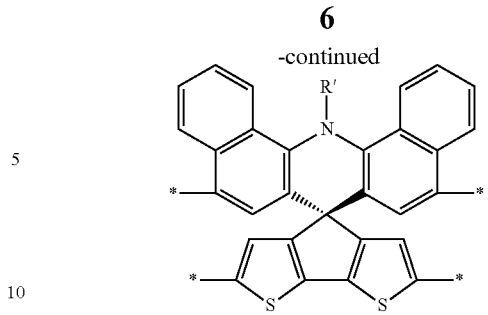

wherein, the related alkyl chain R' can also be introduced on the nitrogen atom, and n' is a natural number ranging from 1 to 10. Their specific structures are as follows:

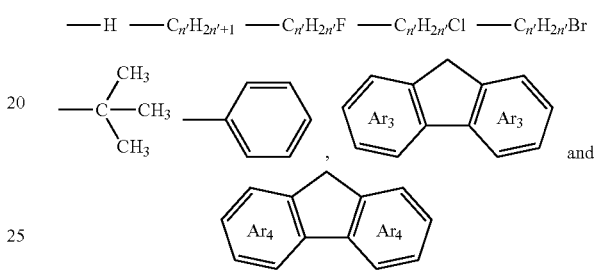

They are identical or different and are one of the following structures:

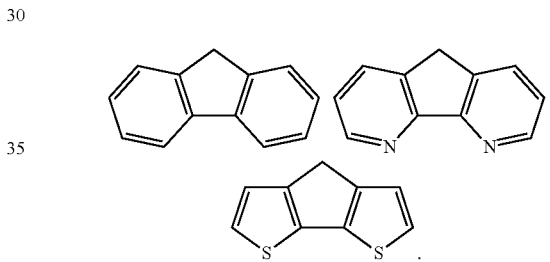

The above-mentioned alkyl chains include: 1) straight chains: a hydrogen atom, alkane chains, alkoxy chains, or alkane chains introducing halogen atoms onto the terminals, such as fluorine, chlorine and bromine; 2) branched chains: tert-butyl chains and branched alkyl chains with oxygen atoms; wherein, m is a natural number ranging from 1 to 10. Their specific structures are as follows:

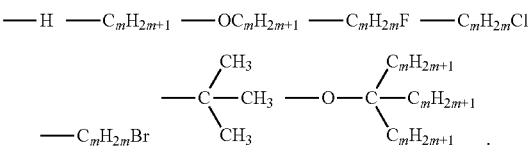

The preparation method of the organic polyspiralgrid nanopolymer material, as described in the present invention, is characterized by: The organic nanopolymer formed by connecting rigid organic mono-spiralgrids through common spiral rings comprises at least two types of fluorene-like groups, of which one is a 9-phenylfluorenol derivative and the other is a spiral ring structure with a geometric configuration similar to that of spirobifluorene; its synthesis method is to make A2B2-type spiral ring-containing synthon have Friedel-Crafts reaction in a dry organic solvent at room temperature under the catalysis of an acid as the catalyst to get the organic polyspiralgrid nanopolymer through common spiral rings, and then make A1B1-type spiral ring-containing synthon have Friedel-Crafts reaction to seal the terminals of the above organic polyspiralgrid nanopolymer to get the final structure. The structural formula of the organic polyspiralgrid nanopolymer as well as its reaction formula are as follows:

Beneficial effects: The structures of oligomers and polymers were characterized with the nuclear magnetic resonance (NMR), the matrix-assisted laser desorption/ionization time-of-flight mass spectrometry (MALDI-TOF-MS) and gel chromatography (GPC). The thermal stability of the materials was tested with thermogravimetric analysis and

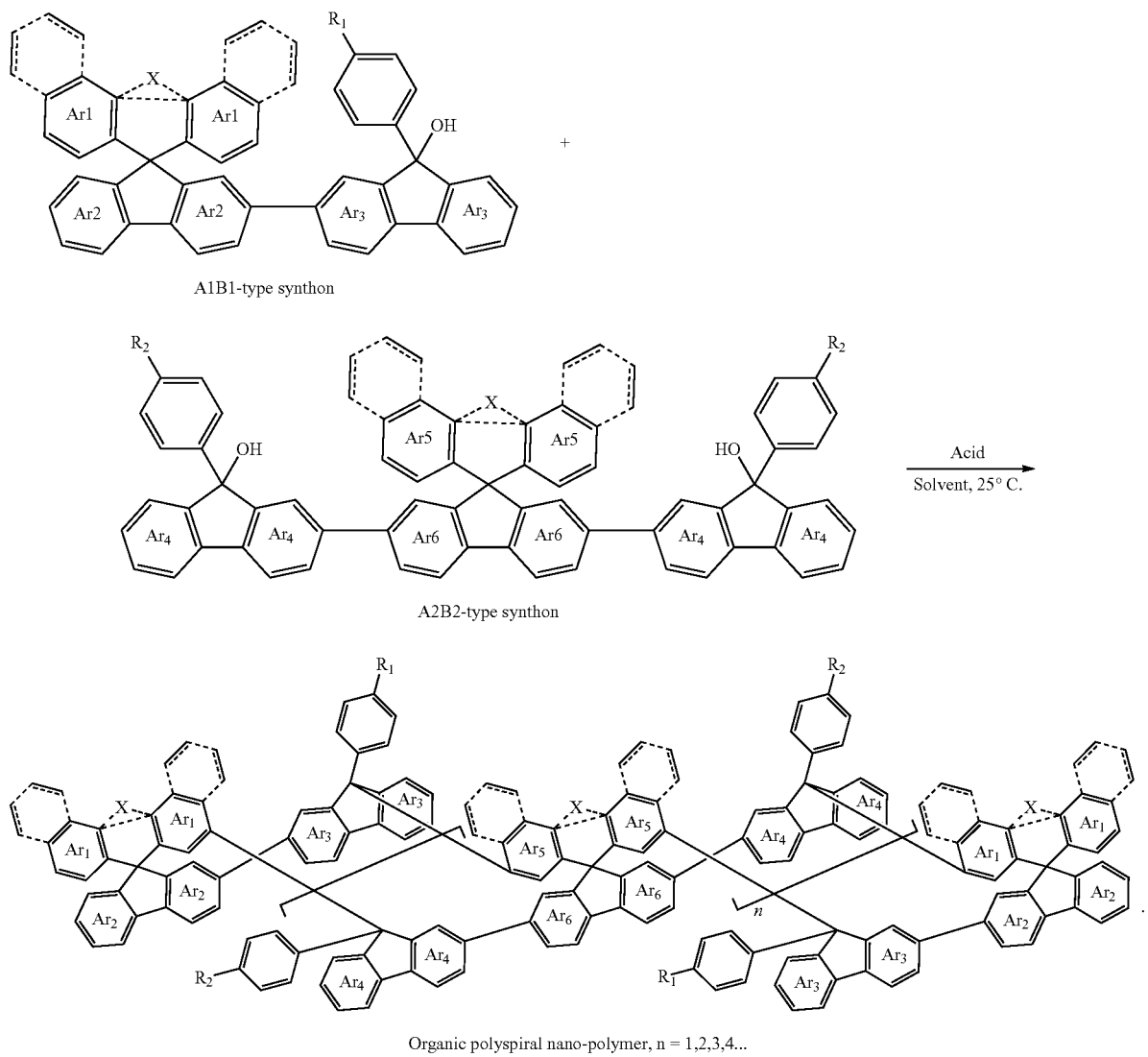

Organic polyspiral nano-polymer, n = 1,2,3,4...

The above-mentioned acid includes Lewis acids and protonic acids, and the amount of acid catalyst added in the reaction is 2-5 times that of A2B2-type synthon according to the reactivity of different substrates; and the reaction concentration of A2B2-type synthon is between 1 mmol/L-10 mmol/L according to the reactivity of different substrates.

The above-mentioned Lewis acids and protonic acids are the combination of one or several of the following acids: acetic acid, hydroiodic acid, hydrobromic acid, hydrochloric acid, methanesulfonic acid, fluoromethylsulfonic acid, trifluoromethanesulfonic acid, concentrated sulfuric acid, trifluoroacetic acid or hydrofluoric acid-antimony pentafluoride.

The above-mentioned dry organic solvent is specifically one of the following solvents: dichlorobenzene, chlorobenzene, dichloromethane, chloroform, 1,2-dichloroethane, nitrobenzene, acetone, tetrahydrofuran and 1,4-dioxane.

differential thermal analysis. The spectral properties of rhombic polymers were characterized with UV-fluorescence spectroscopy.

The main advantages of the present invention are:

(1) The closed-loop polymerization reaction based on Friedel-Crafts reaction has mature reaction conditions, cheap and easily available raw materials, a simple preparation process, mild reaction conditions, high yield, high selectivity and simple post-treatment and is green and non-toxic;

(2) The prepared materials have excellent solubility even when their molecular weight is as high as $1.11 \times 10^5$;

(3) Spiro fluorene and diaryl fluorene have high thermal stability, electrochemical stability and spectral stability;

(4) The stacking interaction of diaryl fluorene has good photoelectric activity.

BRIEF DESCRIPTION OF THE DRAWINGS

FIG. 1a. Proton spectrum of organic bispiralgrid 4a;
FIG. 1b. Mass spectrum of organic bispiralgrid 4a,
FIG. 2a. Proton spectrum of organic polyspiralgrid nanopolymer 5a;
FIG. 4b. Absorption emission spectra of thin films of organic bispiralgrid 4a and organic polyspiralgrid nanopolymer 5a,
FIG. 5a. TG spectrum of organic polyspiralgrid nanopolymer 5a:
FIG. 5b. DSC spectrum of organic polyspiralgrid nanopolymer 5a,
FIG. 6a. CV spectrum of organic bispiralgrid 4a;
FIG. 6b. CV spectrum of organic polyspiralgrid nanopolymer 5a.

DETAILED DESCRIPTION OF THE INVENTION

Figure 1A:
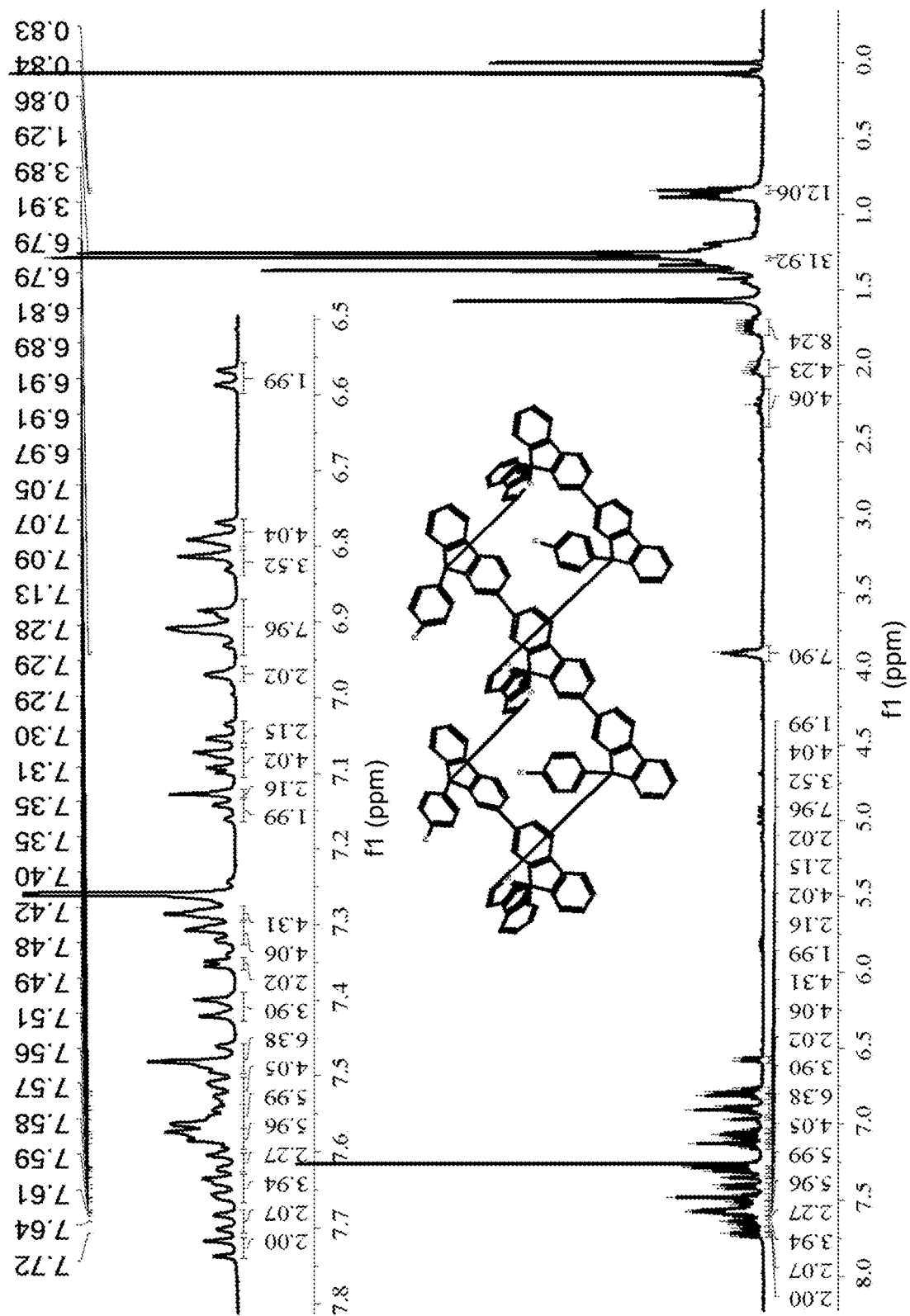
Figure 1B:
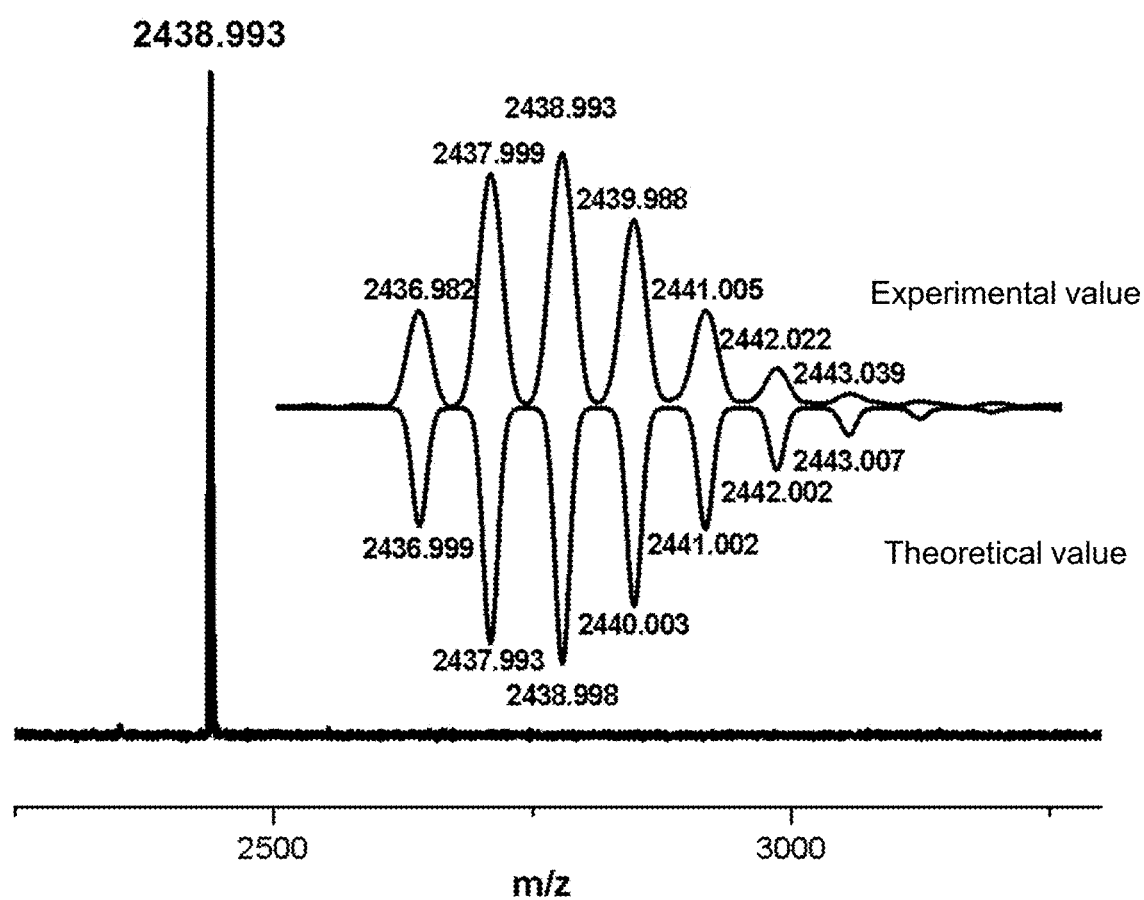
Figure 2A:
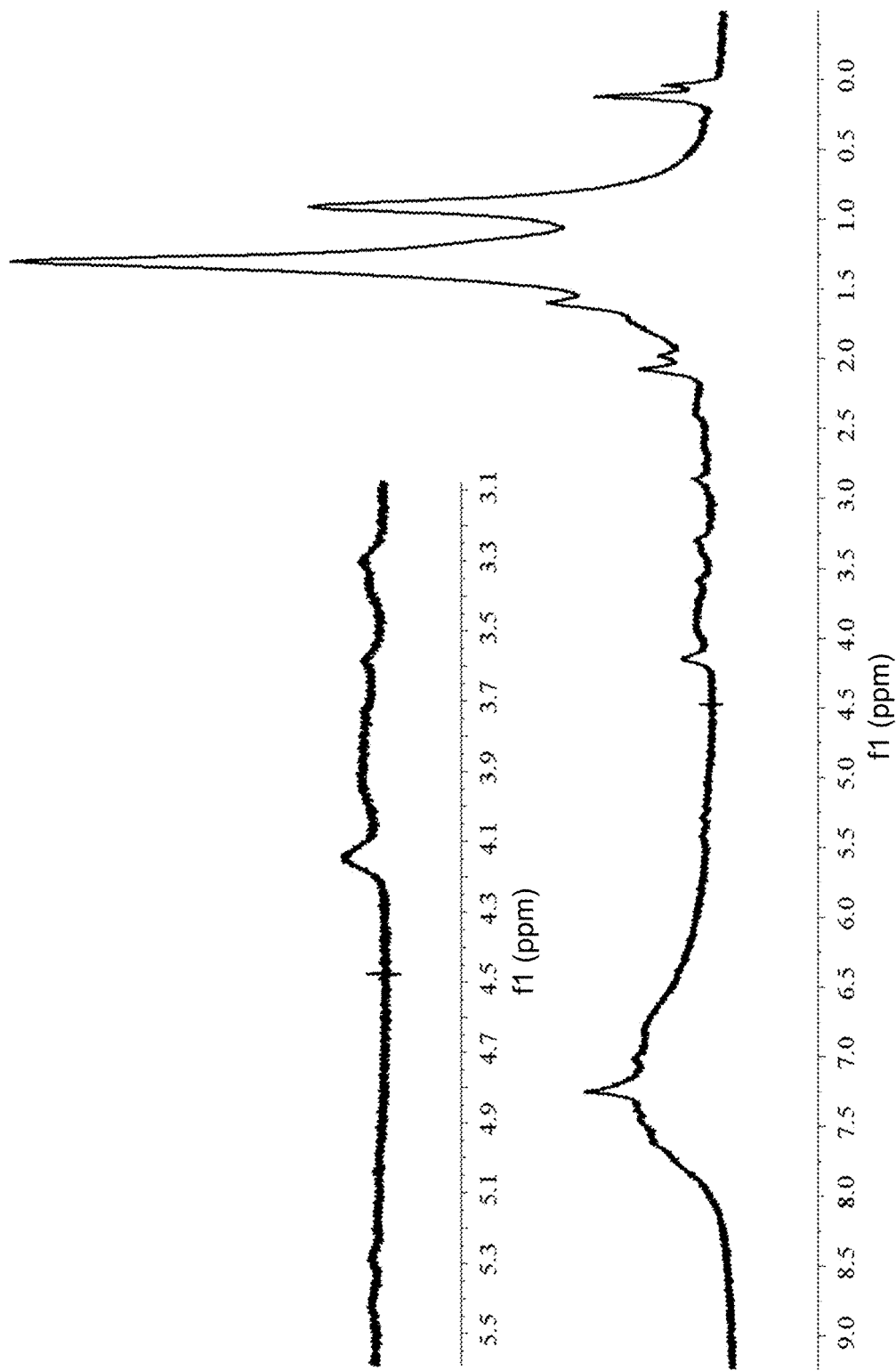
FIG. 2b. Gel chromatogram of organic polyspiralgrid nanopolymer 5a,
FIG. 3. TEM spectrum of organic polyspiralgrid nanopolymer 5a,
FIG. 4a. Ultraviolet absorption and fluorescence emission spectra of organic bispiralgrid 4a and organic polyspiralgrid nanopolymer 5a solutions.
Figure 2B:
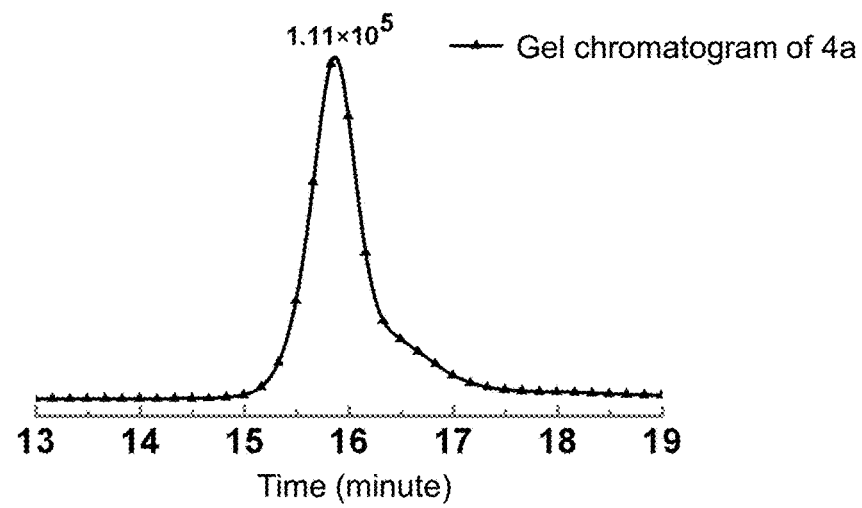
Figure 3:
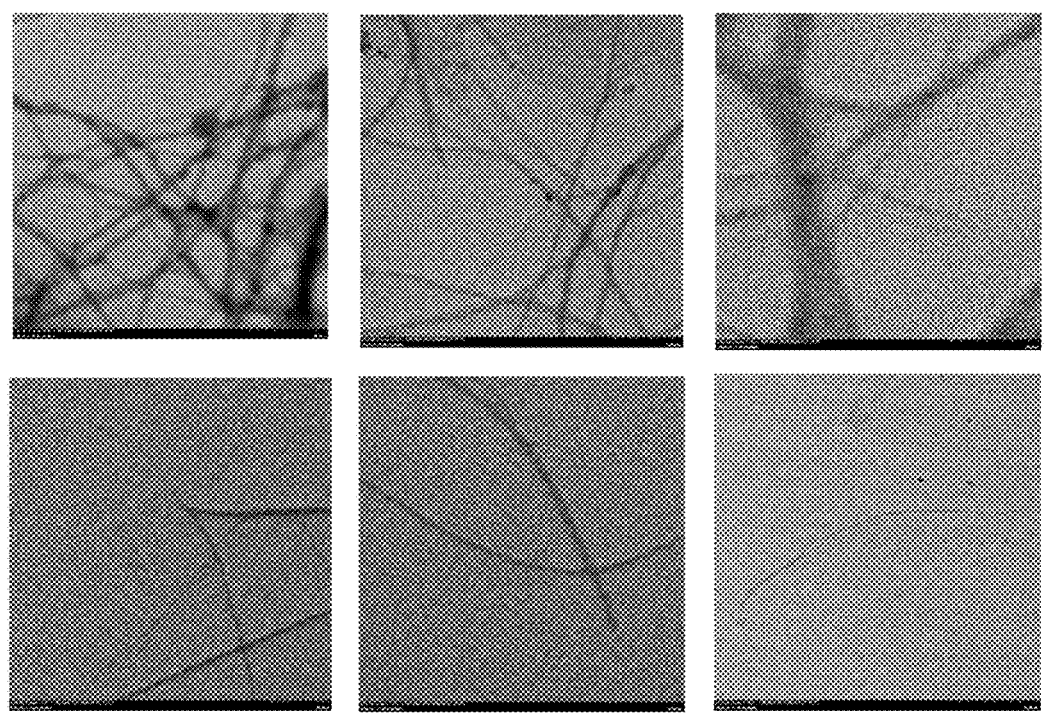
Figure 4A:
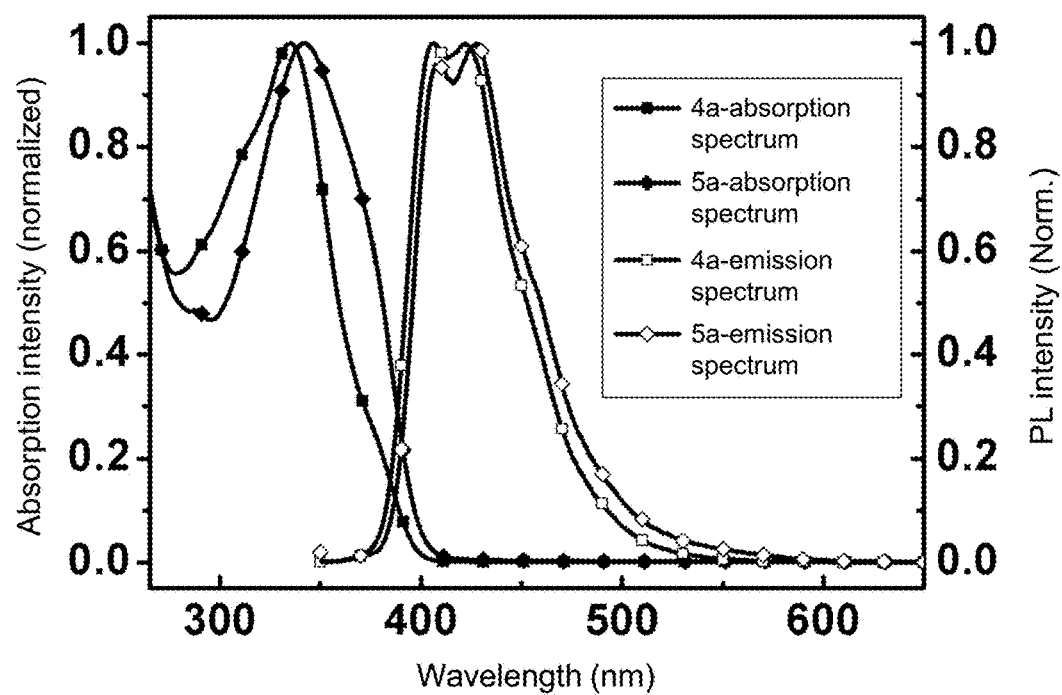
Figure 4B:
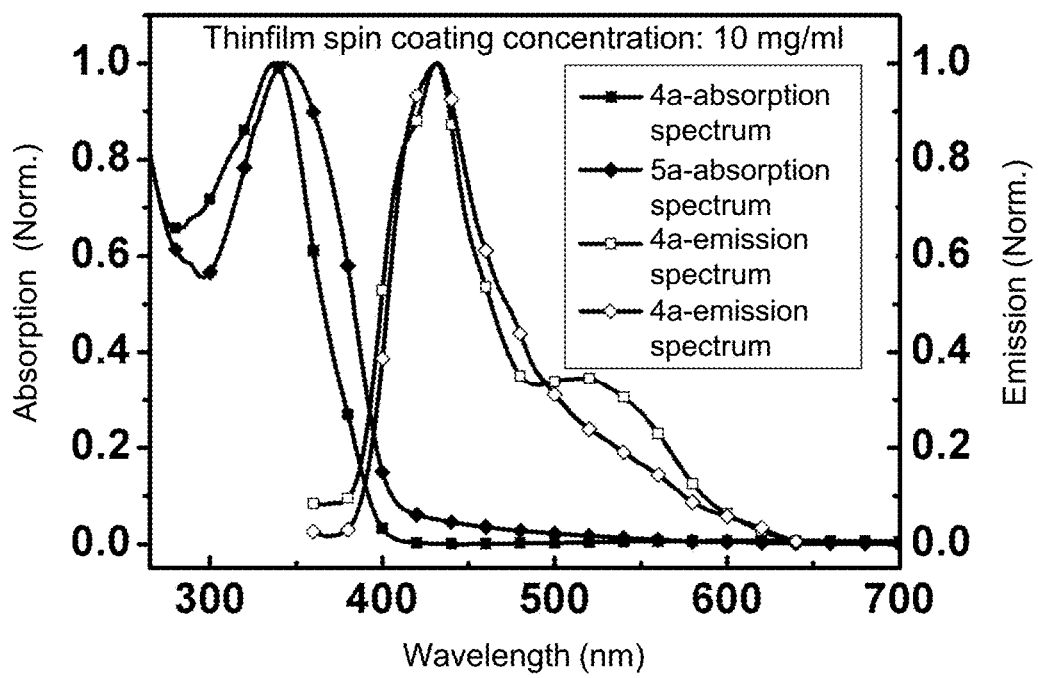
Figure 5A:
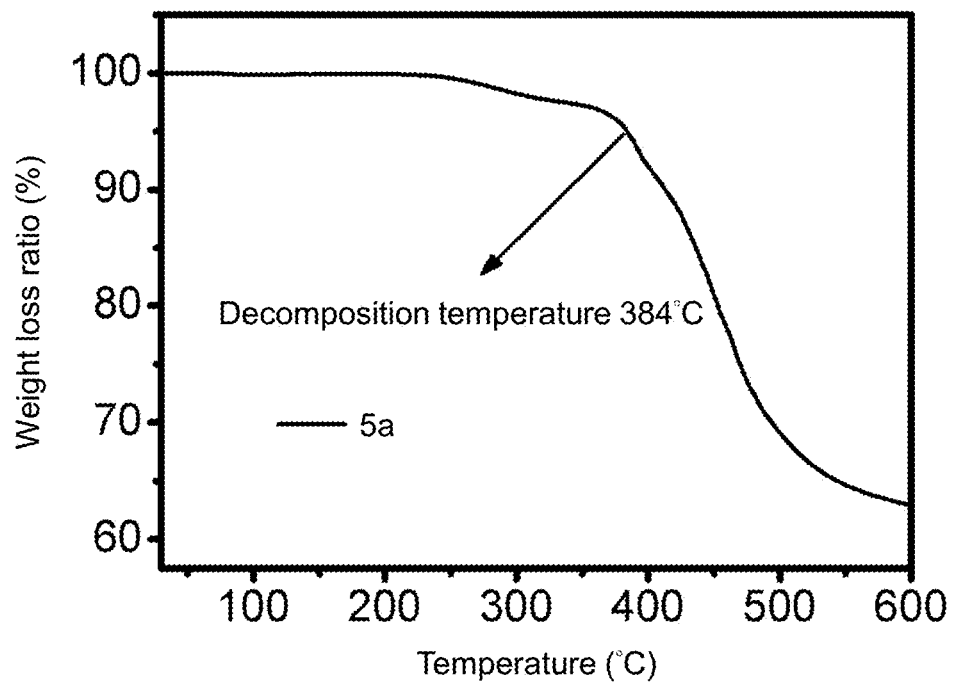
Figure 5B:
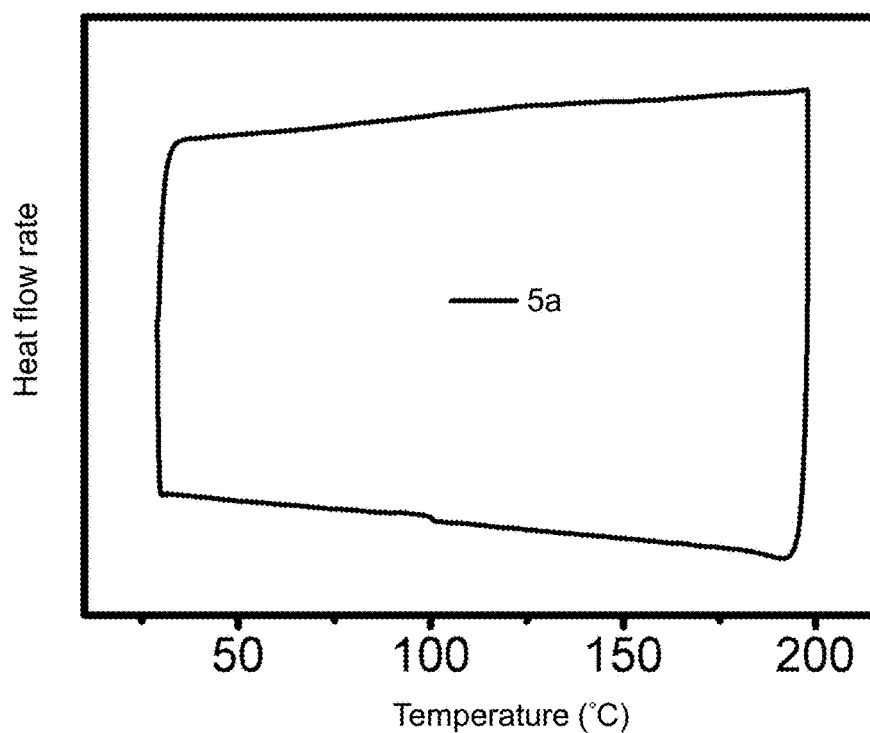
Figure 6A:
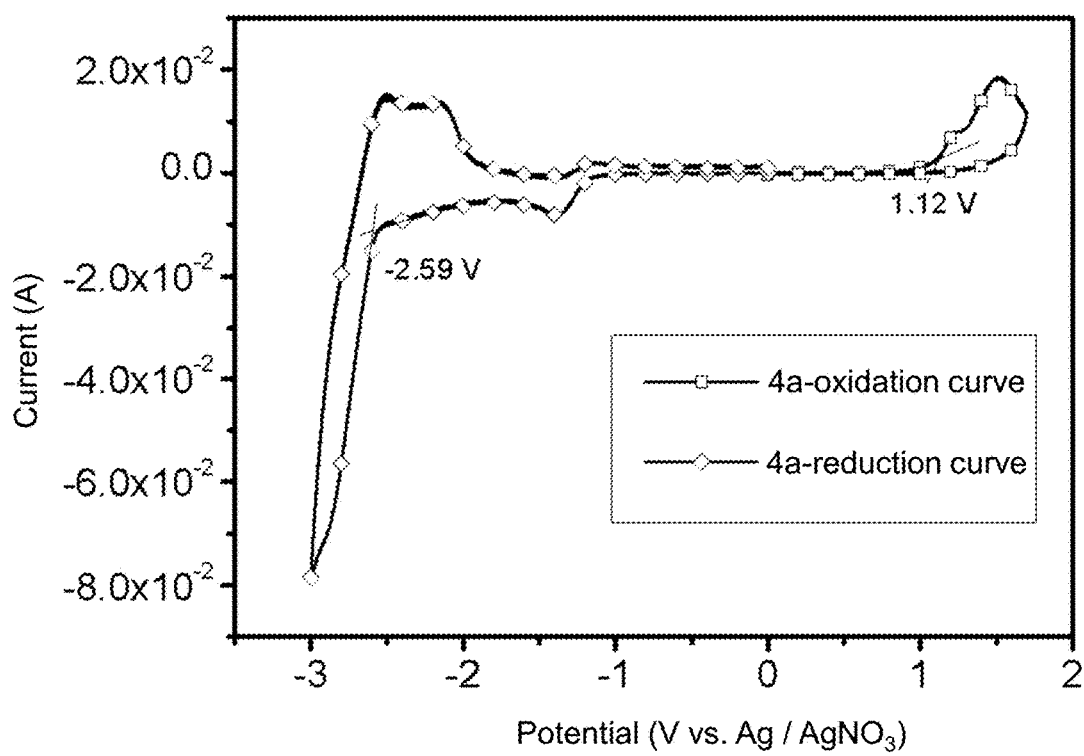
Figure 6B:
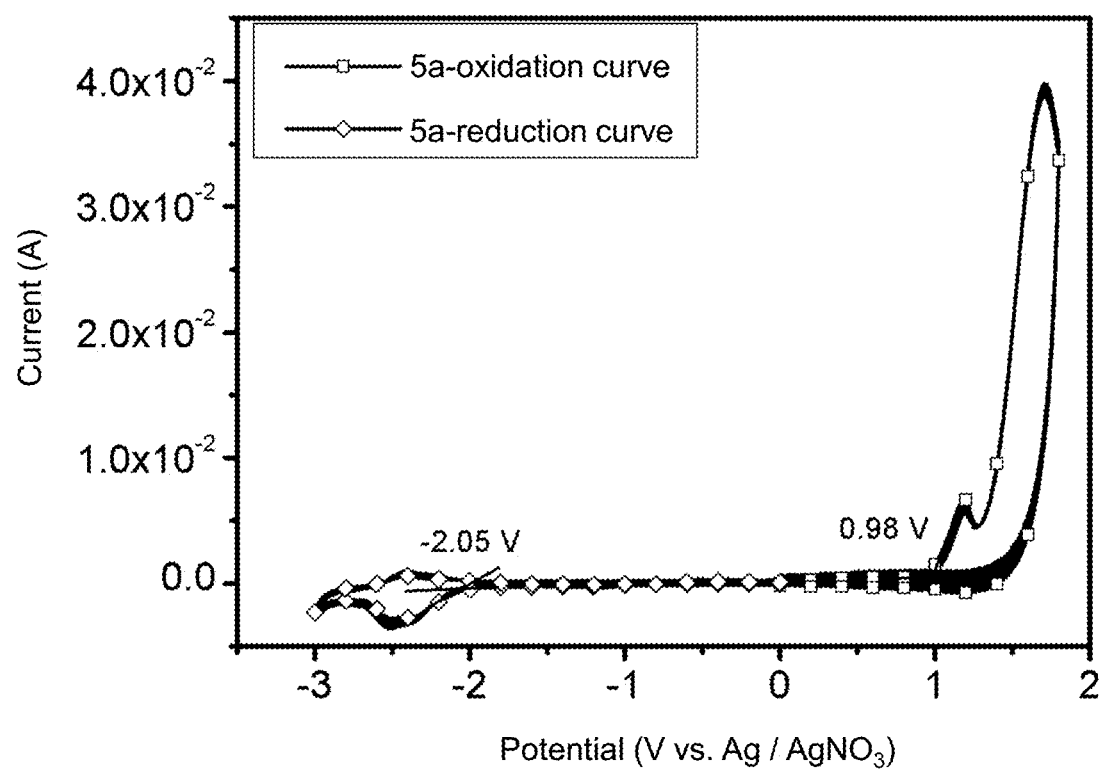

The present invention relates to a type of organic mono-spiralgrid as well as its nanopolymer materials, in which the specific structural formula and reaction route of organic mono-spiralgrid are as follows:

Wherein: $R_1$ is a common alkyl chain, including: 1) straight chains: a hydrogen atom, alkane chains, alkoxy chains, or alkane chains introducing halogen atoms onto the terminals, such as fluorine, chlorine and bromine; 2) branched chains: tert-butyl chains and branched alkyl chains with oxygen atoms; wherein, m is a natural number ranging from 1 to 10. Their specific structures are as follows:

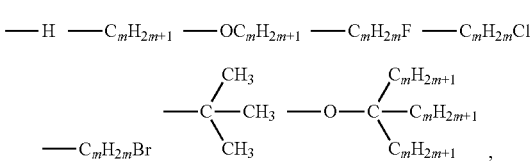

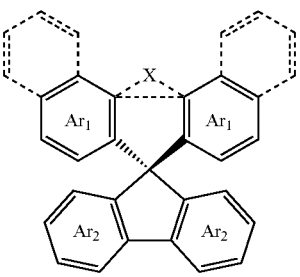

are common fluorene-like spiral ring compounds. Their specific structures are as follows:

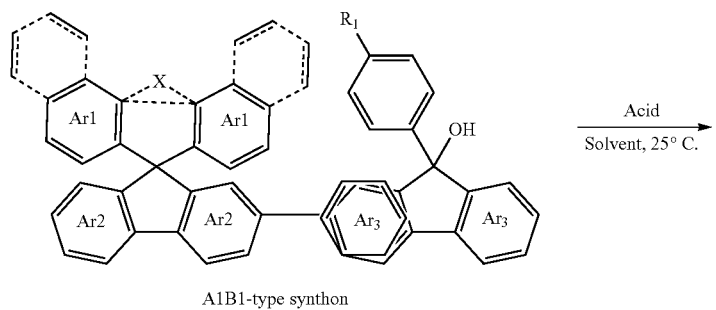

A1B1-type synthon

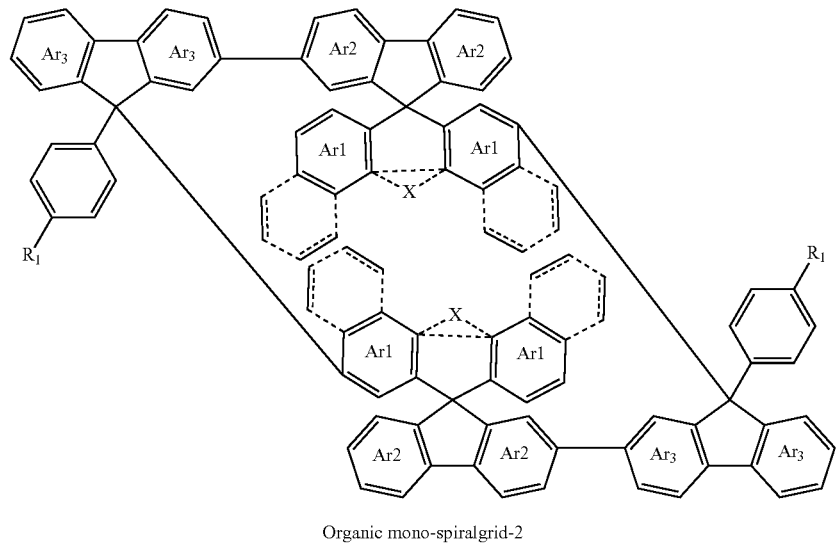

Organic mono-spiralgrid-2

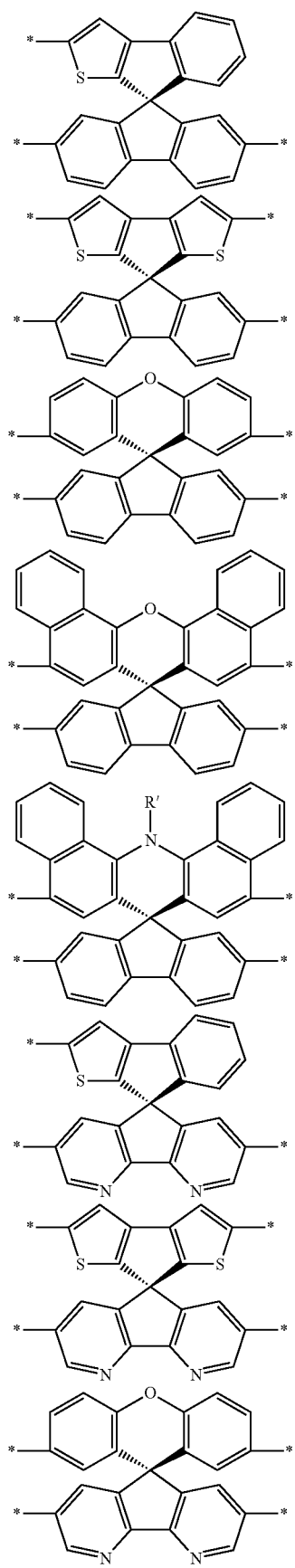
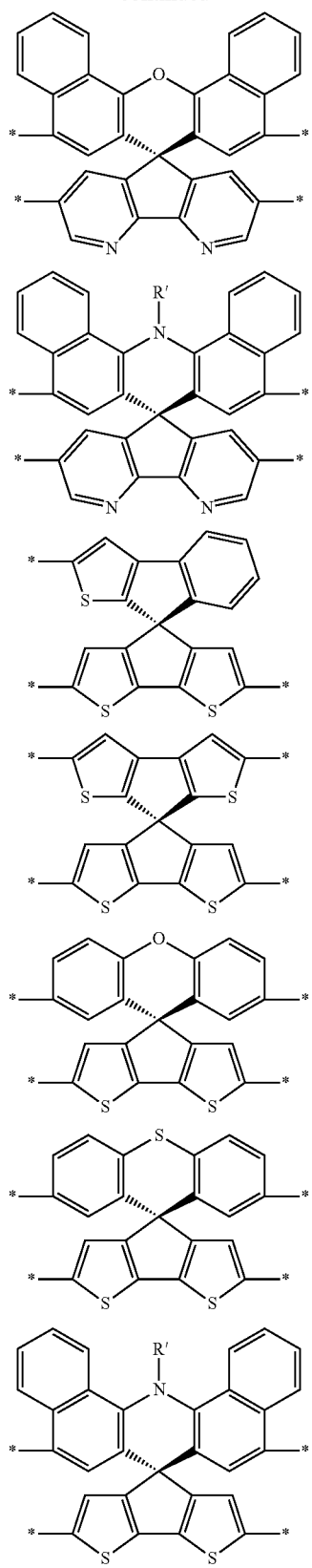
wherein, the related alkyl chain R' can also be introduced on the nitrogen atom, and n' is a natural number ranging from 1 to 10. Their specific structures are as follows:

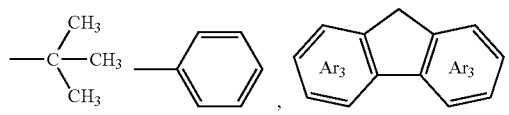

is one of the following structures:

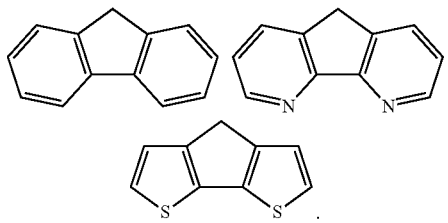

The acid includes Lewis acids and protonic acids. It is the combination of one or several of the following acids: acetic acid, hydroiodic acid, hydrobromic acid, hydrochloric acid, methanesulfonic acid, fluoromethylsulfonic acid, trifluoromethanesulfonic acid, concentrated sulfuric acid, trifluoroacetic acid or hydrofluoric acid-antimony pentafluoride.

The amount of acid catalyst added in the reaction is 2-5 times that of A1B1-type synthon according to the reactivity of different substrates.

The solvent is a dry organic solvent, which is specifically one of the following solvents: dichlorobenzene, chlorobenzene, dichloromethane, chloroform, 1,2-dichloroethane, nitrobenzene, acetone, tetrahydrofuran and 1,4-dioxane. The reaction concentration of A1B1-type synthon is between 1 mmol/L-10 mmol/L according to the reactivity of different substrates.

The specific synthesis steps of the above-mentioned organic mono-spiralgrid are as follows: Take a fixed amount of acid and add it into a round bottom flask containing a fixed amount of dry organic solvent; fully dissolve the spiral ring-containing A1B1-type synthon-1 in another part of dry organic solvent and add it dropwise into the round bottom flask at a rate of 1 drop per second; stir the reaction for 24 h until the reaction substrate is completely reacted, and then add water to quench the neutralization reaction. Extract the resulted mixture solution with dichloromethane, put dichloromethane extracts in the organic phase together, dry them with anhydrous magnesium sulfate, filter off the desiccant, and remove the solvent with vacuum distillation. Separate the crude product through a silica gel chromatography column to obtain the corresponding target product: organic mono-spiralgrid-2.

Its organic bispiralgrid structure as well as its reaction route are as follows:

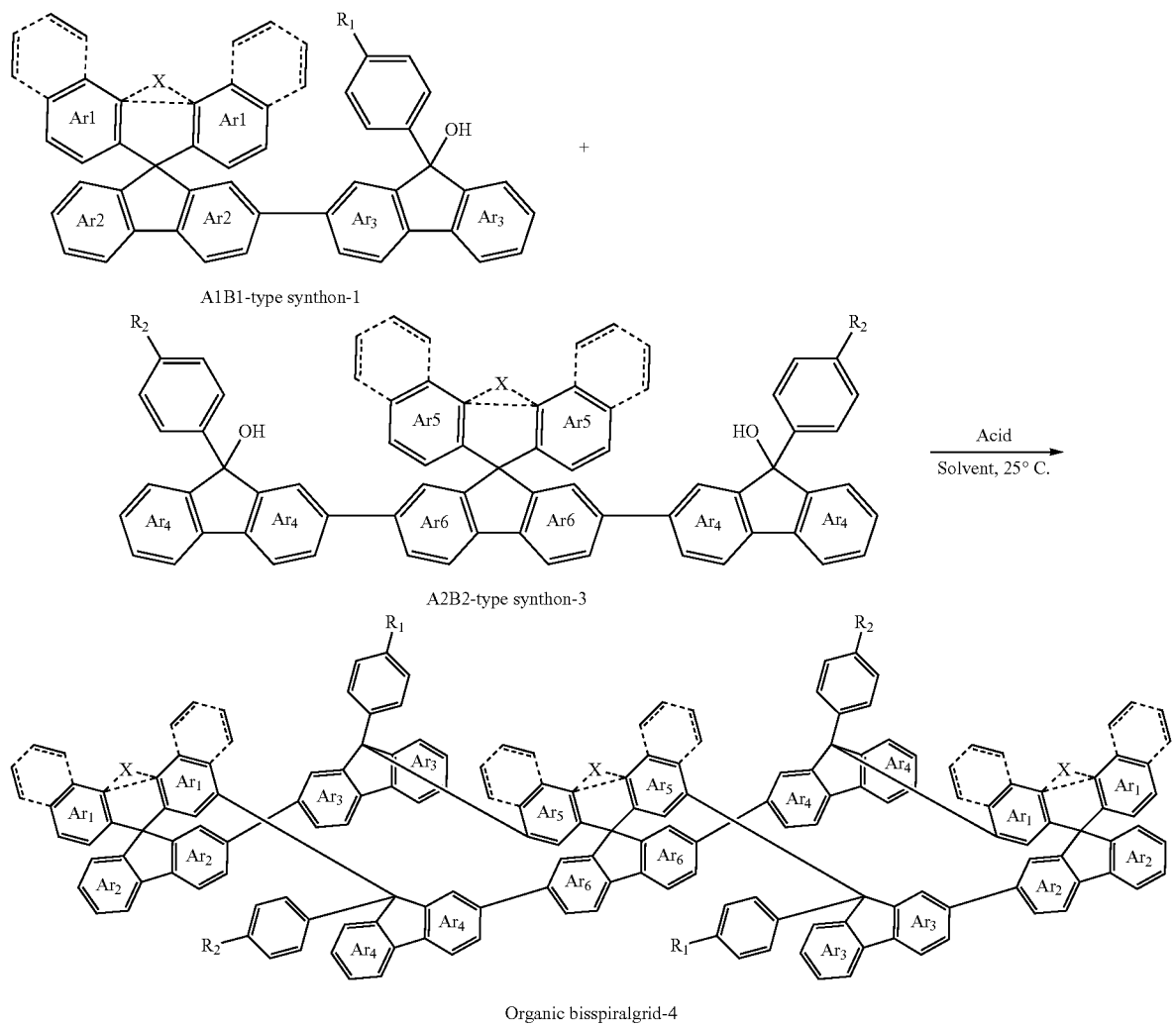

Wherein, $R_1$ and $R_2$ are identical or different, and they are common alkyl chains, including 1) straight chains: a hydrogen atom, alkane chains, alkoxy chains, or alkane chains introducing halogen atoms onto the terminals, such as fluorine, chlorine and bromine; 2) branched chains: tert-butyl chains and branched alkyl chains with oxygen atoms; wherein, m is a natural number ranging from 1 to 10. Their specific structures are as follows:

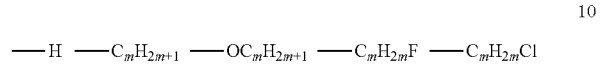

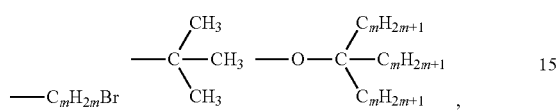

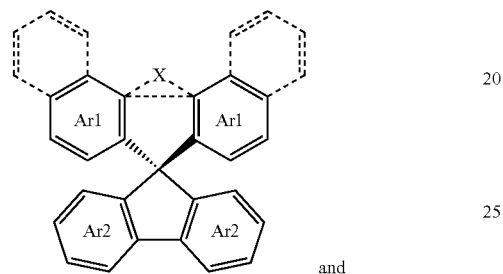

and

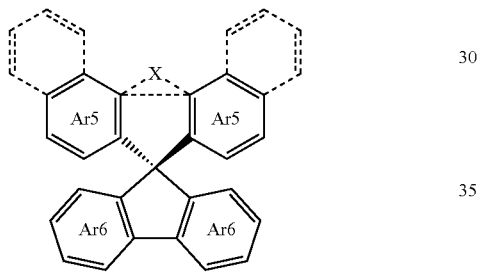

are identical or different and are common fluorene-like spiral ring compounds. Their specific structures are as follows:

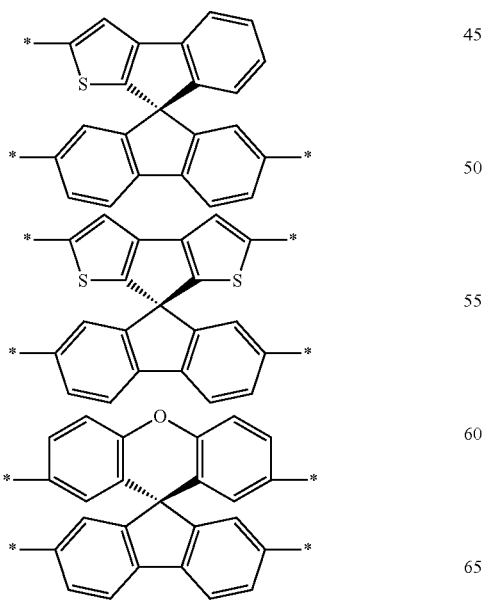

-continued

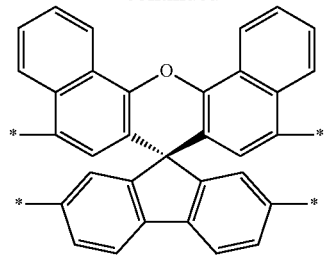

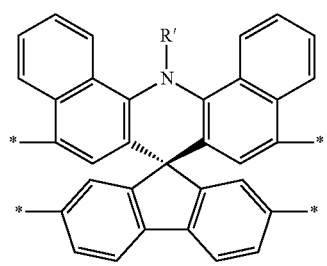

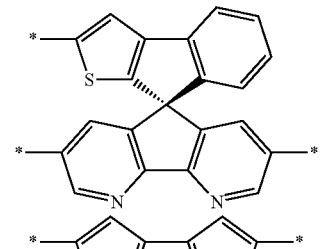

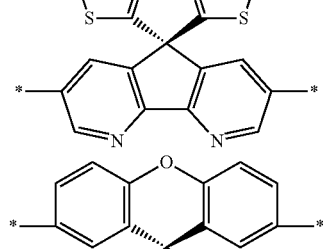

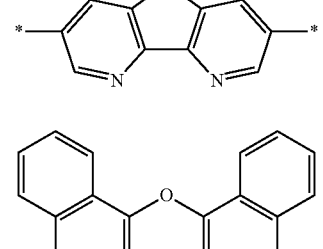

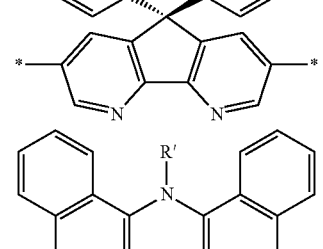

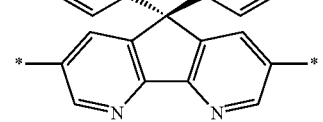

-continued

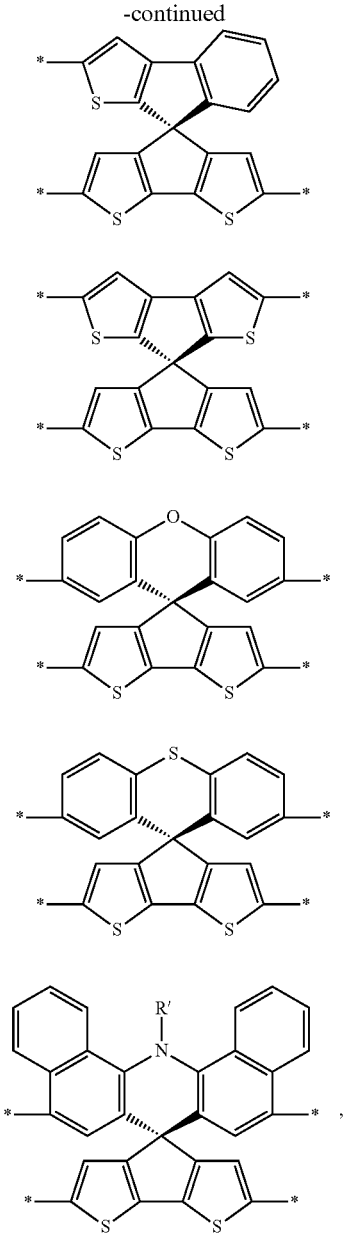

wherein, the related alkyl chain R' can also be introduced on the nitrogen atom, and n' is a natural number ranging from 1 to 10. Their specific structures are as follows:

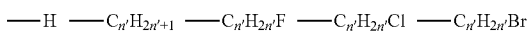

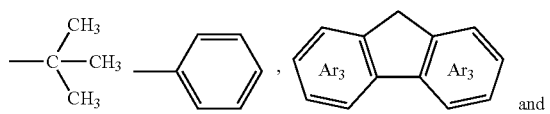

and

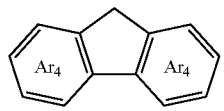

identical or different and are one of the following structures:

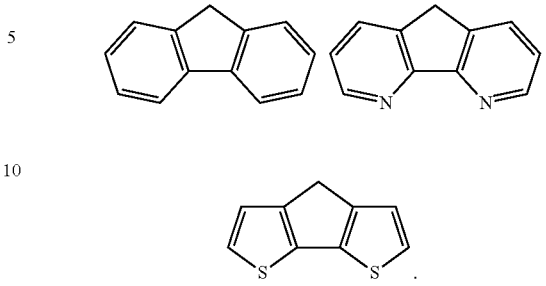

The acid includes Lewis acids and protonic acids. It is the combination of one or several of the following acids: acetic acid, hydroiodic acid, hydrobromic acid, hydrochloric acid, methanesulfonic acid, fluoromethylsulfonic acid, trifluoromethanesulfonic acid, concentrated sulfuric acid, trifluoroacetic acid or hydrofluoric acid-antimony pentafluoride. The amount of acid catalyst added in the reaction is 2-5 times that of A1B1-type synthon according to the reactivity of different substrates.

The solvent is a dry organic solvent, which is specifically one of the following solvents: dichlorobenzene, chlorobenzene, dichloromethane, chloroform, 1,2-dichloroethane, nitrobenzene, acetone, tetrahydrofuran and 1,4-dioxane. The reaction concentration of A1B1-type synthon is between 1 mmol/L-10 mmol/L according to the reactivity of different substrates.

The specific synthesis steps of the above-mentioned organic polyspiralgrid are as follows: Take a fixed amount of acid and add it into a round bottom flask containing a fixed amount of dry organic solvent; fully dissolve the spiral ring-containing A2B2-type synthon-3 in another part of dry organic solvent and add it dropwise into the round bottom flask at a rate of 1 drop per second, and stir the reaction for 1 h-4 h; fully dissolve the spiral ring-containing A1B1-type synthon-1 in another part of dry organic solvent and add it dropwise into the round bottom flask at a rate of 1 drop per second, and stir the reaction for 24 h; then treat the resulted solution with vacuum distillation to remove the solvent until the solution is left to 5 ml, precipitate the remaining solution with methanol, and then extract it with acetone; and take out the solid portion from the mixture and dry it to obtain the corresponding target product: organic polyspiralgrid nanopolymer-5.

The technical solution of the present invention is further described below with reference to the embodiment cases, but these embodiment cases are not limited to the embodiment mode of the present invention. The present invention has several different embodiment modes and is not limited to what is described in this specification. Without departure from the spirit of the present invention, all the schemes devised by technicians in the field should be within the scope of the present invention.

Embodiment Case 1: Preparation of Organic Mono-Spiralgrid-2a

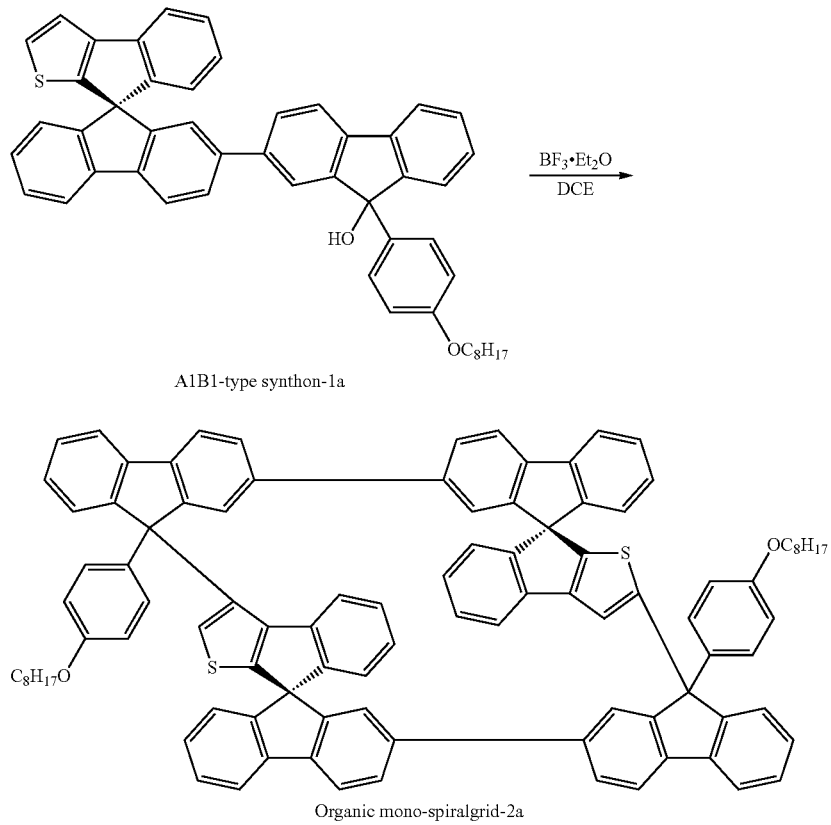

A1B1-type synthon-1a

Organic mono-spiralgrid-2a

Add boron trifluoride ether solution (1 ml) and 400 ml 1,2-dichloroethane to a 1000 ml reaction flask, and stir the mixture evenly; add 1a (0.353 g, 0.5 mmol, 1 equiv) into a constant-pressure dropping funnel containing 100 ml 1,2-dichloroethane, and then add the resulted solution dropwise to the reaction bottle at a rate of one drop per second. After the dropwise addition, the reaction goes on for 5-10 hours. After the reaction is completed, water is added into the reaction solution to quench the reaction. Extract the resulted mixture solution with dichloromethane, put dichloromethane extracts in the organic phase together, dry them with anhydrous magnesium sulfate, filter off the desiccant, and remove the solvent with vacuum distillation. Separate and purify the crude product through a silica gel chromatography column to obtain white solid powder 2a (0.151 g, 43.9%).

$^1$H NMR (400 MHz, CDCl$_3$) δ7.77-7.73; (t, J=7.8 Hz, 4H), 7.66-7.64; (d, J=7.6 Hz, 4H), 7.57-7.52; (t, J=8.0 Hz, 4H), 7.48-7.46; (d, J=8.0 Hz, 2H), 7.42-7.40; (d, J=7.6 Hz, 2H), 7.37-7.36; (m, 5H), 7.34-7.28; (m, 6H), 7.24-7.21; (m, 5H), 7.14-7.10; (t, J=7.2 Hz, 2H), 7.02-6.98; (t, J=7.4 Hz, 2H), 6.89-6.87; (d, J=7.6 Hz, 2H), 6.79-6.72; (d, J=8.8 Hz, 4H), 6.65-6.62; (d, J=8.0 Hz, 4H), 3.89-3.86; (t, J=6.5 Hz, 4H), 1.80-1.73; (m, 4H), 1.46-1.42; (t, J=6.0 Hz, 4H), 1.30-1.27; (m, 16 H), 0.91-0.89; (t, J=4.4 Hz, 6H). $^{13}$C NMR (100 MHz, CDCl$_3$) δ 158.3, 154.8, 152.0, 151.3, 150.8, 148.6, 147.6, 147.3, 145.9, 141.3, 141.1, 140.8, 140.2, 139.3, 139.3, 138.6, 137.8, 128.3, 128.1, 127.9, 127.8, 127.6, 127.4, 126.9, 126.8, 126.1, 125.7, 124.6, 124.4, 123.4, 122.5, 120.2, 120.1, 120.0, 119.2, 117.7, 114.2, 67.9, 64.0, 62.1, 31.9, 31.5, 31.5, 30.3, 30.2, 30.2, 29.7, 29.7, 29.4, 29.3, 26.2, 22.7, 14.2. MALDI-TOF-MS (m/z): 1377.70/1377.55 [M$^+$].

Embodiment Case 2: Preparation of Organic Bispiralgrid-4a

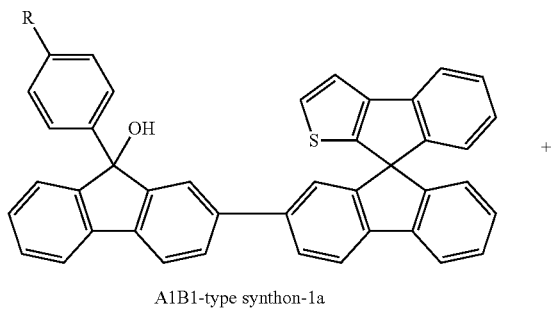

A1B1-type synthon-1a          +

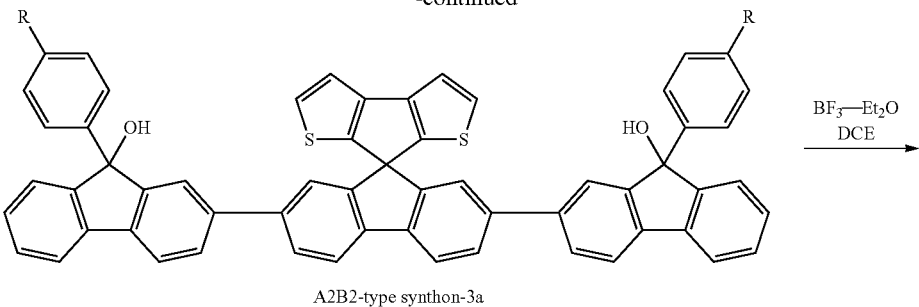

A2B2-type synthon-3a

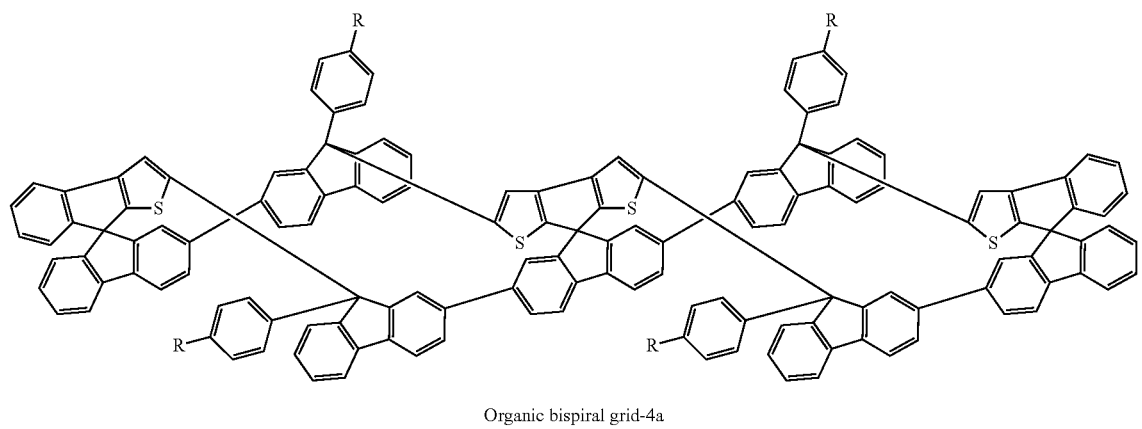

Organic bispiral grid-4a wherein, R=OC$_8$H$_{17}$.

Add boron trifluoride ether solution (1 ml) and 400 ml 1,2-dichloroethane (DCE) to a 1000 ml reaction flask, and stir the mixture evenly; add 1a (0.353 g, 0.5 mmol, 1 equiv) and 3a (0.274 g, 0.25 mmol, 0.5 equiv) into a constant-pressure dropping funnel containing 100 ml 1,2-dichloroethane and mix them evenly until they are completely dissolved, and then add the resulted solution dropwise to the reaction bottle at a rate of one drop per second. After the dropwise addition, the reaction goes on for 5-10 hours. After the reaction is completed, water is added into the reaction solution to quench the reaction. Extract the resulted mixture solution with dichloromethane, put dichloromethane extracts in the organic phase together, dry them with anhydrous magnesium sulfate, filter off the desiccant, and remove the solvent with vacuum distillation. Separate and purify the crude product through a silica gel chromatography column to obtain yellowish solid powder 4a (0.040 g, 6.54%).

$^1$H NMR (400 MHz, CDCl$_3$) δ7.74-7.72; (d, J=8.0 Hz, 2H), 7.70-7.68; (d, J=7.6 Hz, 2H), 7.67-7.64; (d, J=8.0 Hz, 4H), 7.63-7.61; (d, J=8.0 Hz, 2H), 7.59-7.57; (m, 6H), 7.56-7.54; (m, 6H), 7.54-7.51; (d, J=6.4 Hz, 4H), 7.50-7.46; (m, 6H), 7.42-7.40; (d, J=8.8 Hz, 4H), 7.36-7.35; (d, J=2.8 Hz, 2H), 7.32-7.30; (d, J=6.8 Hz, 4H), 7.29-7.28; (m, 4H), 7.16-7.14; (d, J=7.2 Hz, 2H), 7.13; (s, 2H), 7.10-7.07; (d, J=8.4, 2.8 Hz, 4H), 7.06-7.04; (d, J=8.0 Hz, 2H), 6.97 (s, 2H), 6.93-6.89 (m, 8H), 6.83-6.81 (d, J=7.6 Hz, 4H), 6.79-6.77 (d, J=9.2 Hz, 4H), 6.59-6.57; (d, J=8.8 Hz, 2H), 3.91-3.88; (t, J=5.8 Hz, 8H), 2.31-2.21; (m, 4H), 2.06-1.97; (m, 4H), 1.79-1.70; (m, 8H), 1.30-1.29; (m, 32H), 0.86-0.83; (m, 12H). MALDI-TOF-MS (m/z): 2438.99/2439.00 [M$^+$].

Embodiment Case 3: Preparation of Organic Polyspiralgrid Nanopolymer-5a

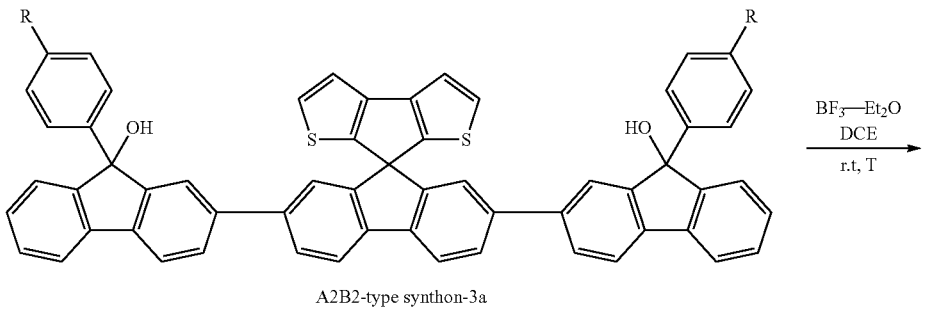

A2B2-type synthon-3a

-continued

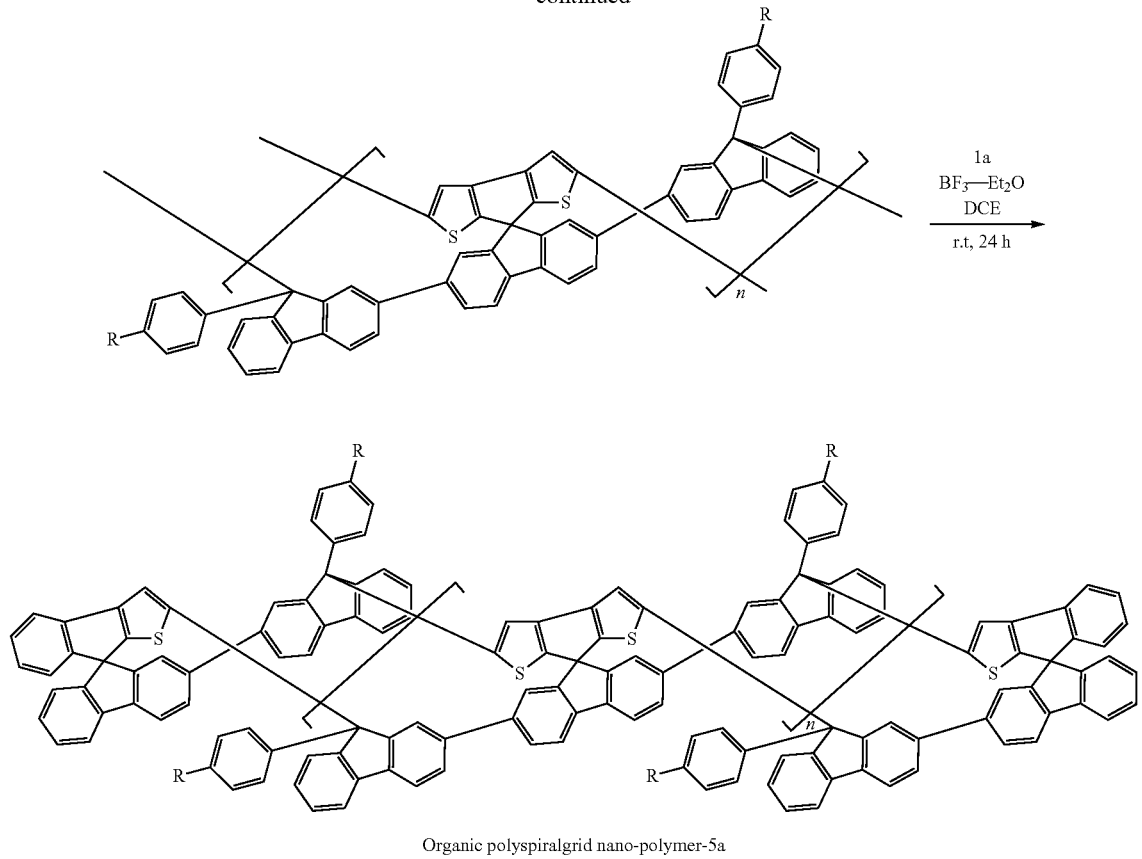

Organic polyspiralgrid nano-polymer-5a wherein, R=OC$_8$H$_{17}$."

At room temperature, take a certain amount of 3a (0.329 g, 0.3 mmol) and dissolve it in 20 ml DCE and then add it dropwise to 40 ml DCE dissolved with boron trifluoride ether solution (0.78 ml, 3 mmol) at a dropping rate of 1 drop per second. After the dropwise addition is completed, the reaction system is stirred for 1-4 hours. Subsequently, 10 ml DCE solution dissolved with 1a (0.021 g, 0.03 mmol) is added dropwise to the reaction system at a dropping rate of 1 drop per second. After the addition is complete, the reaction goes on for 24 hours. After the reaction is completed, the solvent is directly removed with rotary evaporation until 5 ml of the reaction solution is left. The remaining solution is then settled with methanol and filtered. The residue is extracted with acetone in a Soxhlet extractor to obtain a brown product (0.304 g, yield rate 89.8% (the theoretical yield 0.3386 g)).

Embodiment Case 4: Test the Basic Optical, Electrical and Thermal Properties of Organic Mono-Spiralgrid (2a), Organic Bispiralgrid (4a) and Organic Polyspiralgrid Nanopolymer (5a)

A certain amount of sample is taken from each of the three materials and dissolved into a certain amount of dichloromethane (DCM) to form a 10$^{-5}$ mg/mL DCM dilute solution. Shimadzu UV-3150 UV-visible spectrometer and RF-530XPC fluorescence spectrometer are used to measure the absorption spectrum and emission spectrum of the solution. The photoluminescence spectrum of the solution is measured at the ultraviolet (UV) wavelength at which the solution has the maximum UV absorption. The solid film is prepared with the solution spin-coating film forming technology, and the spin-coating solution is a 10 mg/mL chloroform solution. Shimadzu DTG-60H is used for thermogravimetric analysis, and Shimadzu DSC-60A is used for differential scanning thermal analysis. Electrochemical tests are performed with the cyclic voltammetry (CV) through the CHI660E system at room temperature. The typical three-electrode system composed of a working electrode, a platinum wire electrode and a silver nitrate electrode is used in the tests. All the electrochemical tests are performed in a nitrogen atmosphere. The sample is dropped on a glassy carbon electrode to form film on the electrode. After the film is air-dried, the electrode is inserted into tetrabutylammonium hexafluorophosphate (0.1 mol/L)/acetonitrile for testing. The scanning rate is 0.1 V/s. According to the redox starting potential of the CV measurement, the highest occupied molecular orbital (HOMO)/lowest unoccupied molecular orbital (LUMO) ratio of the materials is calculated based on the reference energy level of ferrocene (4.8 eV lower than vacuum): HOMO/LUMO=−($E_{ox/red}$−0.03 V)−4.8 eV, where 0.03 V is the standard potential difference of ferrocene relative to Ag/Ag$^+$.

What is claimed is:
1. An organic polyspiralgrid nanopolymer material represented by the following structure formula:

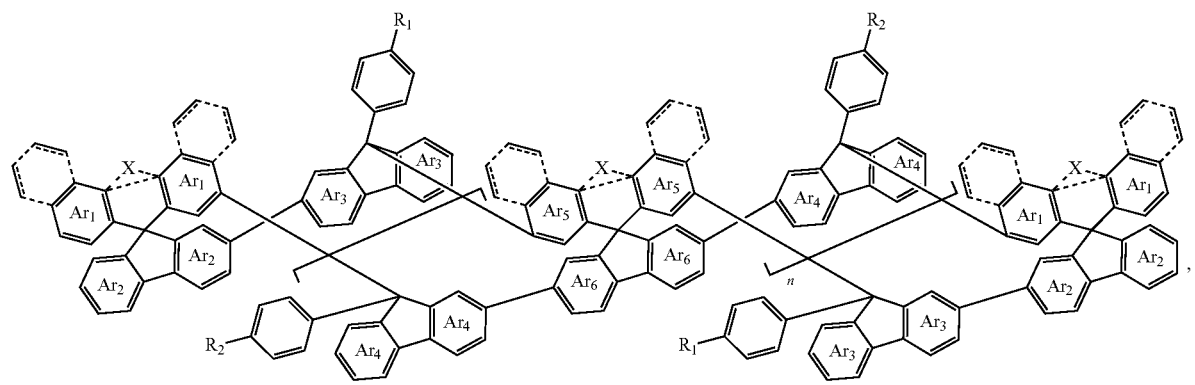
wherein, $R_1$ and $R_2$ are identical or different, and are selected from the following groups:
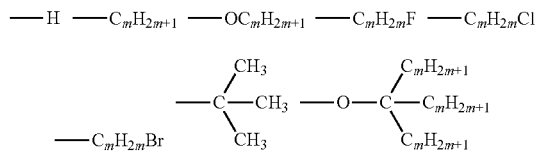
wherein, m is a natural number ranging from 1 to 10,
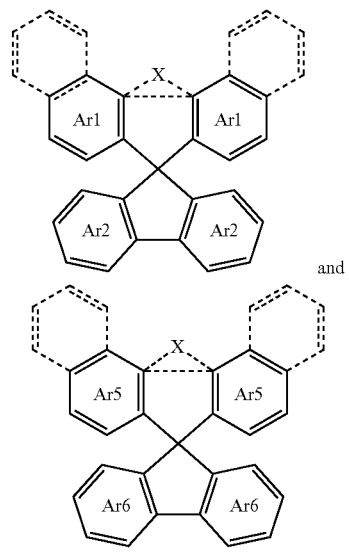
are identical or different and the specific structures thereof are as follows:
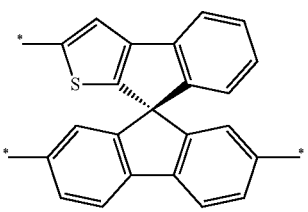
-continued
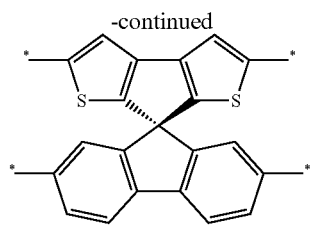
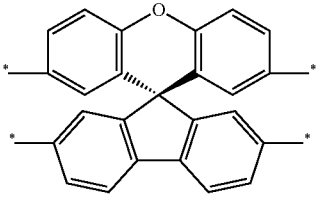
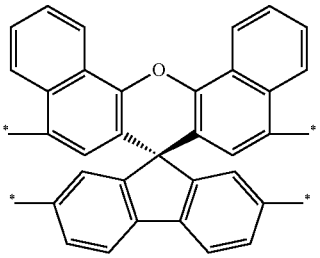
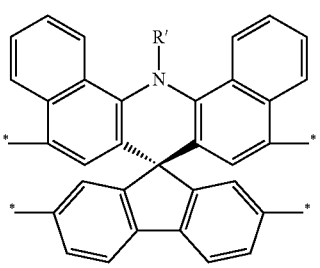
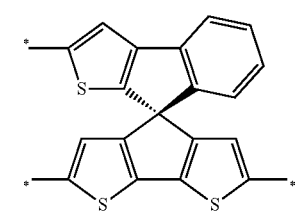

27
-continued
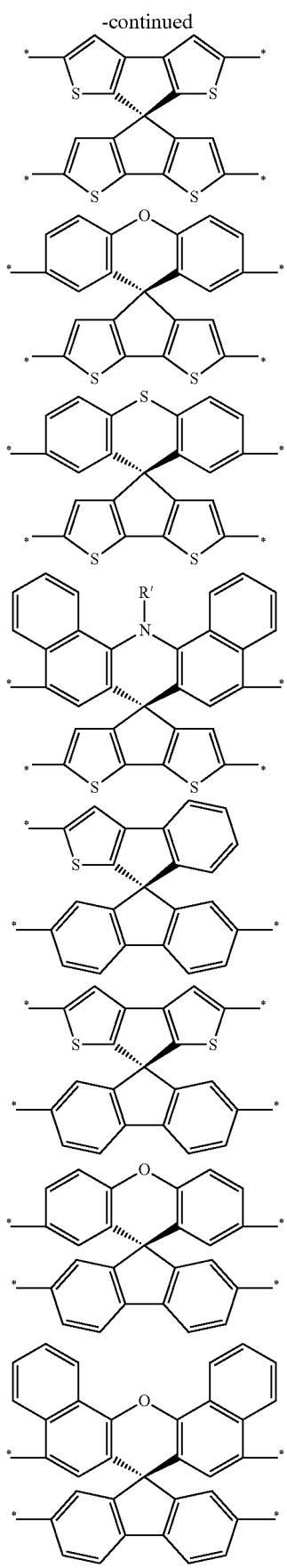
28
-continued
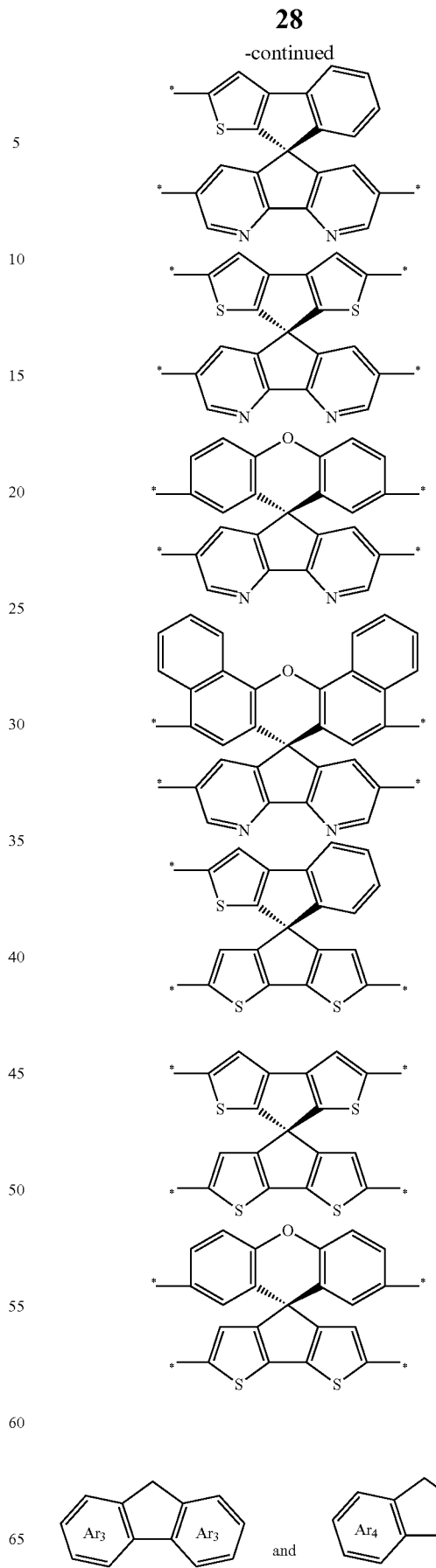

are identical or different and are one of the following structures:

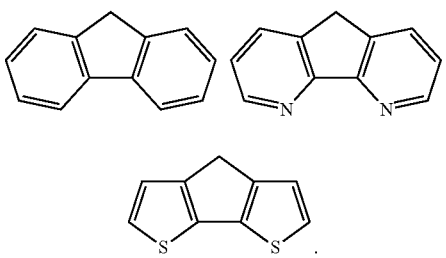

2. A method for preparing the organic polyspiralgrid nanopolymer material of claim 1, comprising forming an organic nanopolymer by connecting rigid organic monospiralgrids through common spiral rings, wherein the polymer comprises at least two types of fluorene-like groups, wherein one type of the fluorene-like groups is a 9-phenylfluorenol derivative and the other type of the fluorene-like groups is a spiral ring structure with a geometric configuration similar to that of spirobifluorene; a synthesis method of the organic nanopolymer is to make A2B2-type spiral ring-containing synthon have Friedel-Crafts reaction in a dry organic solvent at room temperature under the catalysis of an acid as the catalyst to get the organic polyspiralgrid nanopolymer through common spiral rings, and then make A1B1-type spiral ring-containing synthon have Friedel-Crafts reaction to seal the terminals of the organic polyspiralgrid nanopolymer to get the final structure, the structural formula of the organic polyspiralgrid nanopolymer as well as reaction formula of the organic polyspiralgrid nanopolymer are as follows:

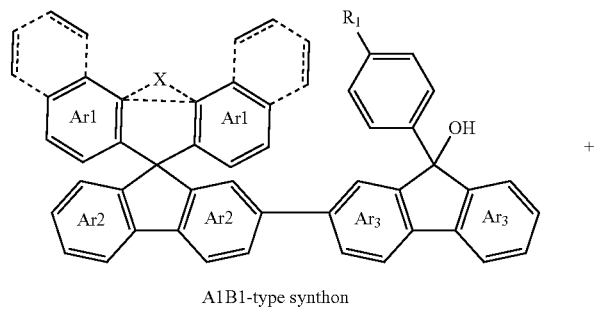

A1B1-type synthon

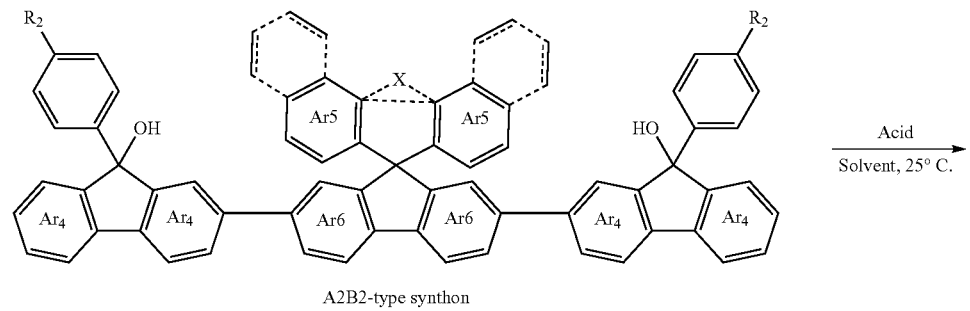

A2B2-type synthon

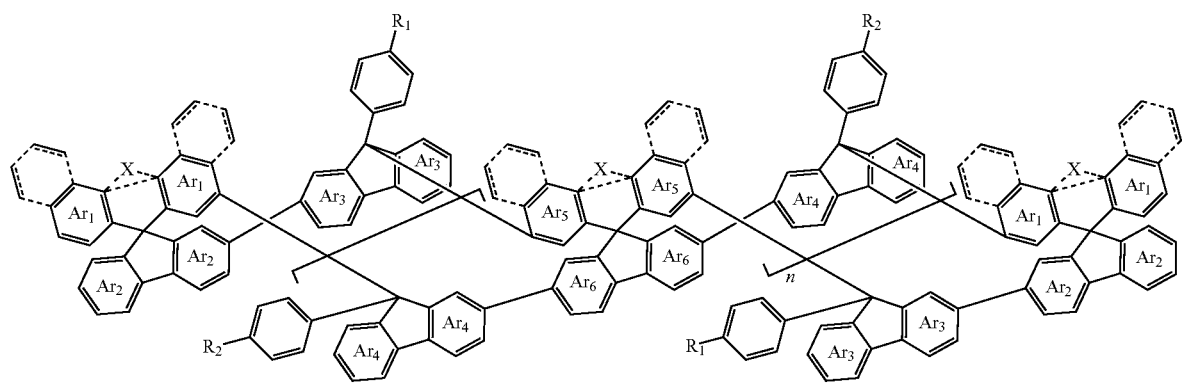

Organic polyspiral nano-polymer, n = 1,2,3,4...

3. The method for preparing the organic polyspiralgrid nanopolymer material of claim 2, wherein the acid includes Lewis acids and protonic acids, and an amount of acid catalyst added is 2-5 times that of A2B2-type synthon according to reactivity of different substrates; and a reaction concentration of A2B2-type synthon is between 1 mmol/L-10 mmol/L according to the reactivity of different substrates.

4. The method for preparing the organic polyspiralgrid nanopolymer material of claim 3, wherein the Lewis acids and protonic acids are one or a combination of several of the following acids: acetic acid, hydroiodic acid, hydrobromic acid, hydrochloric acid, methanesulfonic acid, fluoromethylsulfonic acid, trifluoromethanesulfonic acid, concentrated sulfuric acid, trifluoroacetic acid and hydrofluoric acid-antimony pentafluoride.

5. The method for preparing the organic polyspiralgrid nanopolymer material of claim 2, wherein the dry organic solvent is one of the following solvents: dichlorobenzene, chlorobenzene, dichloromethane, chloroform, 1,2-dichloroethane, nitrobenzene, acetone, tetrahydrofuran and 1,4-dioxane.

* * * * *